US006803232B1

(12) United States Patent
Herzog (10) Patent No.: US 6,803,232 B1
(45) Date of Patent: Oct. 12, 2004

(54) NPY-Y7 RECEPTOR GENE

(75) Inventor: Herbert Herzog, New South Wales (AU)

(73) Assignee: The Garvan Institute of Medical Research, Darlinghurst (AU)

( * ) Notice: Subject to any disclaimer, the term of this patent is extended or adjusted under 35 U.S.C. 154(b) by 0 days.

(21) Appl. No.: 09/719,088

(22) PCT Filed: Jun. 29, 1999

(86) PCT No.: PCT/AU99/00523

§ 371 (c)(1),
(2), (4) Date: Dec. 8, 2000

(87) PCT Pub. No.: WO00/00606

PCT Pub. Date: Jan. 6, 2000

(30) Foreign Application Priority Data

Jun. 29, 1998 (AU) .............................. PP 4385

(51) Int. Cl.[7] .................................. C12N 5/00
(52) U.S. Cl. ...................... 435/325; 536/23.1; 536/23.5
(58) Field of Search ............................. 435/325, 320.1, 435/348, 358, 369; 536/23.1, 23.5, 23.6

(56) References Cited

U.S. PATENT DOCUMENTS

| 4,256,832 A | 3/1981 | Findl et al. |
| 4,655,834 A | 4/1987 | Haruta et al. |
| 5,273,880 A | 12/1993 | Schiestl |

FOREIGN PATENT DOCUMENTS

| DE | 19549417 | 6/1997 |
| EP | 0281298 | 9/1988 |
| EP | 0273771 | 9/1993 |
| EP | 0808899 A2 | 11/1997 |
| EP | 0821061 A2 | 1/1998 |
| EP | 0834563 A2 | 4/1998 |
| EP | 0854191 A2 | 7/1998 |
| EP | 0872550 A2 | 10/1998 |
| EP | 0881289 A2 | 12/1998 |
| EP | 0884387 A | 12/1998 |
| FR | 2775694 | 9/1999 |
| JP | 7191037 | 7/1995 |
| JP | 8205708 | 8/1996 |
| WO | WO93/23534 | 11/1993 |
| WO | WO95/21191 | 8/1995 |
| WO | WO 96/34877 | 11/1996 |
| WO | WO96/38725 | 12/1996 |
| WO | WO97/38308 | 10/1997 |
| WO | WO98/03534 | 1/1998 |
| WO | WO98/03539 | 1/1998 |
| WO | WO98/07030 | 2/1998 |
| WO | WO98/44149 | 10/1998 |
| WO | WO98/56820 | 12/1998 |
| WO | WO99/42582 | 8/1999 |
| WO | WO99/53092 | 10/1999 |
| WO | WO99/58567 | 11/1999 |
| WO | WO99/58568 | 11/1999 |
| WO | WO99/64021 | 12/1999 |
| WO | WO99/64452 | 12/1999 |
| WO | WO00/04045 | 1/2000 |
| WO | WO00/12105 | 3/2000 |
| WO | WO00/12106 | 3/2000 |
| WO | WO00/12175 | 3/2000 |
| WO | WO00/31107 | 6/2000 |

OTHER PUBLICATIONS

Biochem.Biophys.Res.Comm. 256, pp. 352–6 (1999) "Sequence and tissue distribution of a novel G–protein–coupled receptor expressed prominently in human placenta." Cikos, W. et al.
Trends in Neuroscience 20(7) pp. 294–298 (1997) "Y–receptor subtypes–how many more?" Blomqvist, A.G. and Herzog, H.
Eishourbagy et al., "Receptor for the Pain Modulatory Neuropeptides FF and AF is an Orphan G Protein–coupled Receptor", *J. Biol. Chem*, vol. 275 No. 34, Aug. 25, 2000, pp. 25965–25971.
Kotani et al., "Functional characterization of a human receptor for neuropeptide FF and related peptides", *Br J. Pharmacology 2001 133*, pp. 138–144.
Gribkoff et al., "Phase Shifting of Circadian Rhythms and Depression of Neuronal Activity in the Rat Suprachiasmatic Nucleus by Neuropeptide Y: Mediation by Different Receptor Subtypes", *Journal of Neurscience, Apr. 15, 1998*; pp. 3014–3022.
Hagan et al., "Effect of Peptide YY (PYY) of Food–Associated Conflict", *Physiology & Behavior, vol. 58, No. 4*, pp. 731–735; 1995.
Morley et al., "Peptide YY (PYY), a potent orexigenic agent", *Brain Research*, 341 (1985), pp. 200–203.
Kaye et al., "Neurochemistry of Bullmia Nervosa", *J Clin Psychiatry 1991; 52 (10, suppl)*; pp. 21–28.
Parker et al., "Melecular cloning and characterization of GPR74 a novel G–protein coupled receptor closest related to the Y–receptor family"; *Molecular Brain Research 77 (2000)*; pp. 199–208.
Bonini et al., "Identification and Characterization of Two G Protein–coupled Receptors for Neuropeptide FF", *J Biological Chemistry, 2000, vol. 275, No. 50, Dec. 15*; pp. 39324–39331.
Hinuma et al., "New neuropeptides containing carboxy–terminal Rfamide and their receptor in mammals", *Nature Cell Biology, vol. 2, Oct. 2000*, pp.703–708.
Zajac, "Neuropeptide FF: new molecular insights", *TRENDS in Pharmacological Sciences, vol. 22, Feb. 2001*; p. 63.
Liu et al., "Identification and characterization of two cognate receptors for mammalian FMRFamide–like neuropeptides", *NCBI Accession No. AF330053*, 2001.
Liu et al., "Direct Submission", *NCBI Accession No. AAK94197*, 2001.

*Primary Examiner*—Dave T. Nguyen
*Assistant Examiner*—Jon Eric Angell
(74) *Attorney, Agent, or Firm*—Clark & Brody (57) ABSTRACT

The invention provides isolated polynucleotide molecules encoding a novel neuropeptide Y (NPY) receptor (designated NPY-Y7). These isolated polynucleotide molecules can be used to express the receptor in cells which can then be used to screen compounds for agonist and antagonist activity.

11 Claims, 4 Drawing Sheets

FIGURE 1

Human neuropeptide Y - Y7 sequence alignment

Human-Mouse NPY Y7 Receptor Alignment

```
hy7    1 MFIMNEKWDTNSSENWHPIWNVNDTKHHLYSDINITYV  38
mY7    1 MSTMSEKWDSNSSESWNHIWSGNDTQHHWYSDINITYV  38 hy7   39 NYVLHQPQVAAIFIISYFLIFFLCMMGNTVVCFIVMRN  76
mY7   39 NYVLHQPQVAAVFISSYLLIFVLCMVGNTVVCFIVIRN  76 hy7   77 KHMHTVTNLFILNLAISDLLVGIFCMPITLLDNIIAGW  114
mY7   77 RHMHTVTNFLILNLAISDLLVGIFCMPITLLDNIIAGW  114 hy7  115 PFGNTMCKISGLVQGISVAASVFTLVAIAVDRFQCVVY  152
mY7  115 PFGSSMCKISGLVQGISVAASVFTLVAIAVDRFRCVVY  152 hy7  153 PFKPKLTIKTAFVIIMIIWVLAITIMSPSAVMLHVQEE  190
mY7  153 PFKPKLTVKTARVTIVIIWGLAIAMTPSAIMLHVQEE  190 hy7  191 KYYRVRLNSQNKTSPVYWCREDWPNQEMRKYLTVLFA  228
mY7  191 KYYRVRLSSHNKTSTVYWCREDWPRHEMRRYLTVLFA  228 hy7  229 NIYLAPLSLIVIMYGRIGISLFRAAVPHTCRKNQEQWH  266
mY7  229 IIYLAPLSLIVIMYARICASDFKTAAHCTG--KQRPVQ  264 hy7  267 VVSRKKQKIIKMLLIVALLFILSWLPLWTLMMLSDYAD  304
mY7  265 CMYQEKQKVIKMLLTVALLFILSWLPDWTLMMLSDYTD  302 hy7  305 LSPNELQTINIYITYPFAHWLAFGNSSVNPLIYGFFNEN  342
mY7  303 LSPNKLRTINIYITYPFAHWLAFCNSSVNPLIYGFFNEN  340 hy7  343 FRRGFQEAFQLQLCQKRAKPMEAYTLKASHVLINTSN  380
mY7  341 FRNGFQDAFQI--CQKKAKPQEAYSIRAKRNIVINTSG  376 hy7  381 QLWQESTFQNPHGETLYRKSAENLRNRN           408
mY7  377 LLWQEPVSQNPGCENLGCGKSADNPHRNP          405
```

NPY-Y7 RECEPTOR GENE

FIELD OF INVENTION

The present invention relates to isolated polynucleotide molecules which encode a novel neuropeptide Y (NPY) receptor designated NPY-Y7. In addition, the present invention relates to the use of these molecules in the production of NPY-Y7 receptors using recombinant DNA technology and to methods of screening and testing compounds for agoinist or antagonist activity.

BACKGROUND OF THE INVENTION

Neuropeptide Y (NPY) forms a family (called the pancreatic polypeptide family) together with pancreatic polypeptide (PP) and peptide YY (PYY), which all consist of 36 amino acids and possess a common tertiary structure. NPY receptors, members of the G protein- coupled receptor superfamily, when activated influence a diverse range of important physiological parameters, including effects on psychomotor activity, central endocrine secretion, anxiety, reproduction, vasoactive effects on the cardiovascular system and strongly stimulates food consumption. Specific agonists and antagonists of NPY are therefore likely to be of substantial benefit for therapy of a wide range of clinical disorders. As NPY possess a compact tertiary structure and different parts of the molecule are required for interaction with different subtypes of the receptor, the logical developments of both agonists and antagonists is critically dependent upon the availability and knowledge of specific receptor structure.

It is presently known that NPY binds specifically to at least six receptors; Y1, Y2, Y3, Y4, Y5 (or "atypical Y1") and Y6. While it has been demonstrated that NPY receptors couple to the adenylate cyclase second messenger system, it remains probable that additional NPY receptor subtypes exist since there is evidence that phosphatidylinositol turnover, cations, and arachidonic acid may also function as second messengers for NPY.

Since NPY agonists and antagonists may have commercial value as, for example, potential anti-hypertensive agents, cardiovascular drugs, neuronal growth factors, anti-psychotics, anti-obesity and anti-diabetic agents, the ability to produce NPY receptors by recombinant DNA technology would be advantageous. To this end, DNA molecules encoding Y1, Y2, Y4, Y5 and Y6 have previously been isolated.

The present inventors have now isolated novel DNA molecules encoding the human and murine NPY-Y7 receptors.

SUMMARY OF THE INVENTION

Thus, in a first aspect, the present invention provides an isolated polynucleotide molecule encoding an NPY-Y7 receptor or a functionally equivalent fragment thereof.

The encoded NPY-Y7 receptor is characterised by the N-terminal amino acid sequence:

$MX_1X_2MX_3EKWDX_4NSSE$ (SEQ ID NO: 1), wherein $X_1$, $X_2$, $X_3$ and $X_4$ are selected from codable amino acids but, preferably, $X_1$ is selected from Phe and Ser, $X_2$ is selected from Ile and Thr, $X_3$ is selected from Asn and Ser, and $X_4$ is selected from Thr and Ser.

More preferably, the polynucleotide molecule encodes a human NPY-Y7 receptor of about 408 amino acids or a murine NPY-Y7 receptor of about 405 amino acids.

Most preferably, the polynucleotide molecule encodes a human NPY-Y7 receptor having an amino acid sequence substantially corresponding to that shown as SEQ MD NO: 2 or a murine NPY-Y7 receptor having an amino acid sequence subtantially corresponding to that shown as SEQ E) NO: 3.

The polynucleotide molecule may comprise a nucleotide sequence substantially corresponding or, at least, showing at least 90% (more V preferably, at least 95%) homology to that shown at nucleotides 1 to 1903 or nucleotides 369 to 1592 of SEQ ID NO: 4 or any portion thereof encoding a functionally equivalent NPY-Y7 receptor fragment.

The polynucleotide molecule may be incorporated into plasmids or expression vectors (including viral vectors), which may then be introduced into suitable bacterial, yeast, insect and mammalian host cells. Such host cells may be used to express the NPY-Y7 receptor.

Accordingly, in a second aspect, the present invention provides a mammalian, insect, yeast or bacterial host cell transformed with the polynucleotide molecule of the first aspect.

In a third aspect, the present invention provides a method of producing NPY-Y7 receptors or functionally equivalent fragments thereof, comprising culturing the host cell of the second aspect-under conditions enabling the expression of NPY-Y7 receptors or functionally equivalent fragments thereof.

Preferably, the host cell is mammalian or of insect origin. Where the cell is mammalian, it is presently preferred that it be a Chinese hamster ovary (CHO) cell, monkey kidney (COS) cell or human embryonic kidney 293 cell. Where the cell is of insect origin, it is presently preferred that it be an insect Sf9 cell.

In a preferred embodiment, the NPY-Y7 receptors or functionally equivalent fragments thereof are expressed onto the surface of the host cell.

The polynucleotide molecule of the present invention encodes an NPY receptor which may be of interest both clinically and commercially as it is expressed in many regions of the body and neuropeptides of the NPY family affect a wide number of systems.

By using the polynucleotide molecule of the present invention it is possible to obtain NPY-Y7 receptor protein or fragments thereof in a substantially pure form.

Accordingly, in a fourth aspect, the present invention provides a NPY-Y7 receptor or a functionally equivalent fragment of said receptor, in a substantially pure form.

In a fifth aspect, the present invention provides an antibody or fragment thereof capable of specifically binding to the NPY-Y7 receptor or functionally equivalent fragment of the fourth aspect.

In a sixth aspect, the present invention provides a non-human animal transformed with the polynucleotide molecule of the first aspect of the present invention.

In a seventh aspect, the present invention provides a method for detecting agonist or antagonist agents of an NPY-Y7 receptor, comprising contacting an NPY-Y7 receptor, functionally equivalent fragment thereof or a cell transfected with and expressing the polynucleotide molecule of the first aspect, with a test agent under conditions enabling the activation of an NPY-Y7 receptor, and detecting an increase or decrease in activity of the NPY-Y7 receptor or functionally equivalent fragment thereof.

An increase or decrease in activity of the receptor or functionally equivalent fragment thereof may be detected by measuring changes in cAMP production, $Ca^{2+}$ levels or IP3 turnover after activating the receptor or fragment with specific agonist or antagonist agents.

In a further aspect, the present invention provides an oligonucleotide or polynucleotide probe comprising a nucleotide sequence of 10 or more nucleotides, the probe comprising a nucleotide sequence such that the probe specifically hybridises to the polynucleotide molecule of the first aspect under high stringency conditions (Sambrook et al., *Molecula Cloning: a laboratoy manuiual, Second Edition*, Cold Spring Harbor Laboratory Press).

In a still further aspect, the present invention provides an antisense oligonucleotide or polynucleotide molecule comprising a nucleotide sequence capable of specifically hybridising to an mRNA molecule which encodes an NPY-Y7 receptor so as to prevent translation of the mRNA molecule.

Such antisense oligonucleotide or polynucleotide molecules may include a ribozyme region to catalytically inactivate mRNA to which it is hybridised.

The polynucleotide molecule of the first aspect of the invention may be a dominant negative mutant which encodes a gene product causing an altered phenotype by, for example, reducing or eliminating the activity of endogenous NPY-Y7 receptors.

The term "substantially corresponding" as used herein in relation to amino acid sequences is intended to encompass minor variations in the amino acid sequences which do not result in a decrease in biological activity of the NPY-Y7 receptor. These variations may include conservative amino acid substitutions. The substitutions envisaged are:

G, A, V, I, M; D, E; N, Q; S,T; K, R, H; F, Y, W, H; and P, Nα-alkalamino acids.

The term "substantially corresponding" as used herein in relation to nucleotide sequences is intended to encompass minor variations in the nucleotide sequences which due to degeneracy in the DNA code do not result in a change in the encoded protein. Further, this term is intended to encompass other minor variations in the sequence which may be required to enhance expression in a particular system but in which the variations do not; result in a decrease in biological activity of the encoded protein.

The term "functionally equivalent fragment/s" as used herein is intended to refer to fragments of the NPY-Y7 receptor that exhibit binding specificity and activity that is substantially equivalent to the NPY-Y7 receptor from which it/they is/are derived.

The terms "comprise", "comprises" and "comprising" as used throughout the specification are intended to refer to the inclusion of a stated step, component or feature or group of steps, components or features with or without the inclusion of a further step, component or feature or group of steps, components or features.

Reference to percent homology made in this specification have been calculated using the BLAST program blastn as described by Altschul, S. F. et al., "Capped BLAST and PSI-BLAST: a new generation of protein database search programs", *Nucleic Acids Research*, Vol. 25, No. 17, pp. 3389–3402 (1997).

BRIEF DESCRIPTION OF THE ACCOMPANYING FIGURES

FIG. 1 shows the degree of identity between the predicted amino acid sequence of the human NPY-Y1 (hy1p; SEQ ID NO: 6), NPY-Y2 (hy2p; SEQ ID NO: 7) and NPY-Y7 receptors (hy7p; SEQ ID NO: 2).

FIG. 4 shows the degree of identity between the predicted amino acid sequence of the human NPY-Y7 receptor (hy7; SEQ ID NO: 2) and murine NPY-Y7 receptors (mY7; SEQ ID NO: 3).

DETAILED DISCLOSURE OF THE INVENTION

Human amygdala and testis cDNA libraries (Stratagene) were screened under low strigency conditions with a 401 bp $^{32}$P-labelled fragment (corresponding to nucleotides 507 to 908 of SEQ ID NO: 4) originated from a human fetal brain EST clone (GenBank AA449919). Two overlapping cDNA clones were obtained from the screen. The combined nucleotide sequence (hy7) of the clones is shown as SEQ ID NO: 4 and encodes a protein of 408 amino acids (SEQ ID NO: 2).

Sequence comparison with other G protein coupled receptors identified neuropeptide Y receptors as the most closely related group with approximately 32% amino acid sequence identity to the Y1 receptor subtype (FIG. 1). Further, in situ hybridisation studies of rat brain sections has identified a NPY-Y7 mRNA distribution (expression was found to occur in the amygdala, the CA3 region of the hippocampus and the piriform cortex) which is consistent with,the expression of other NPY-receptor subtypes (Blomquist, A. G., and Herzog, H., TINS 20(7), 1997) and is in agreement with the suggestions of the existence of further Y-receptor family members. This mRNA distribution suggests important functions for the NPY-Y7 receptor in the regulation of the circadian rhythm, anxiety and metabolic status.

Figure 2:
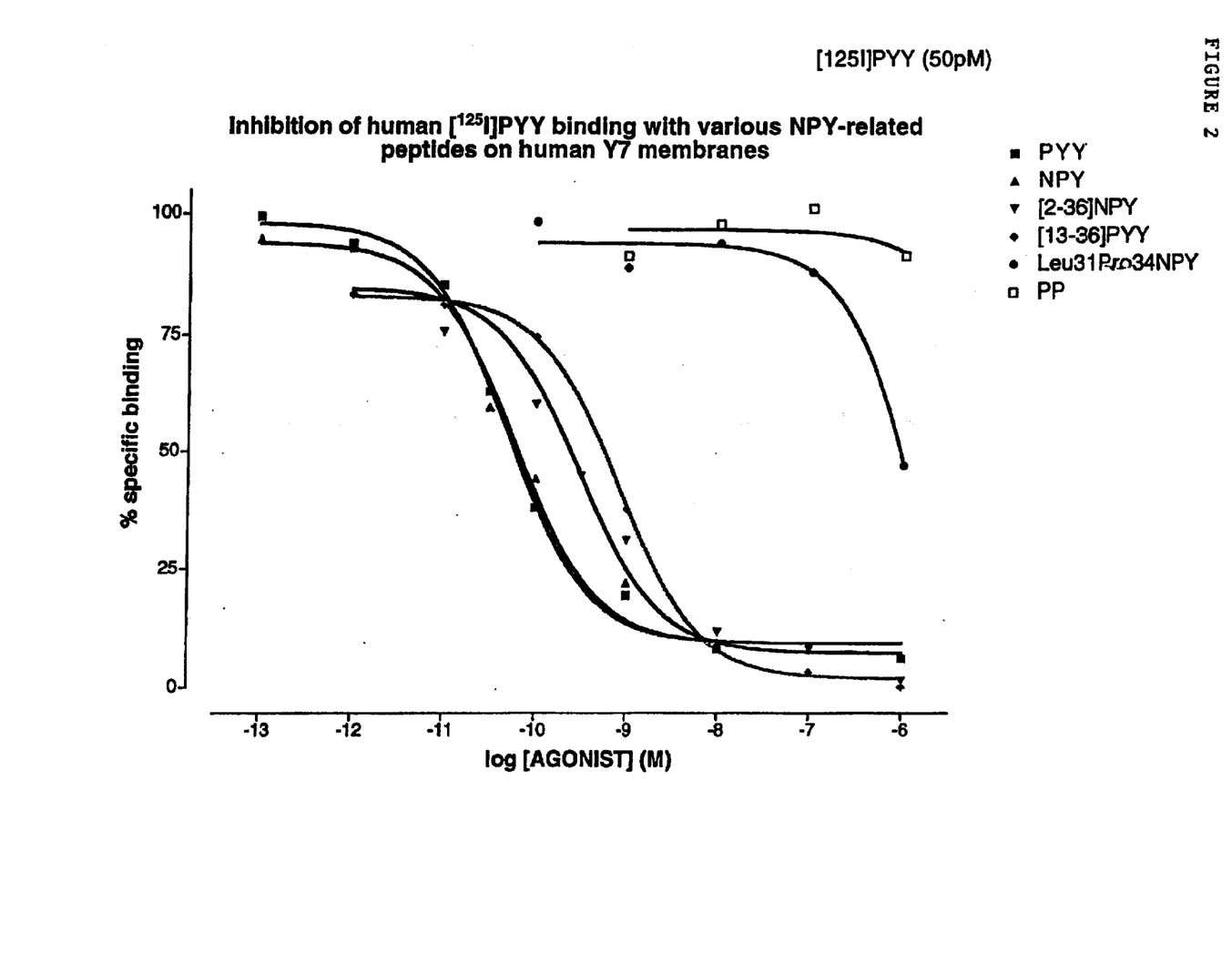
FIG. 2 provides a graph showing the inhibition of human [$^{125}$I]PYY binding with various NPY-related peptides on human NPY-Y7 membranes. The results were obtained through competitive displacement of [$^{125}$I]PYY on membranes of COSm6 cells transiently expressing human NPY-Y7 receptors. Membranes were incubated with [$^{125}$I]PYY (50 pM) and increasing concentrations of peptide competitors. Data are representative of a single experiment with each point measured in triplicate.

Radio-ligand binding experiments has shown that the protein encoded by the hy7 cDNA shows highest affinity for human PYY (FIG. 2). These experiments were conducted using COS-6 or HEX (293) cells transiently expressing recombinant Y7 receptor protein. The radio-ligand binding (Herzog, H. at al., Proc. Natl. Acad. Sci. USA 89:5794–5798, 1992) suggests that the NPY-Y7 receptor has a pharmacology similar to the Y2 receptor (Rose, P., J. Biol. Chem. 270:22661–22664, 1995). The rank of potency for the Y7 receptor is:

PYY>NPY>[2-36]PYY>[3-36]NPY>[13-36]NPY>>(Leu31, Pro34)NPY>PP.

Chromosomal Localisation of the Human Y7 Gene

Screening of a medium resolution Stanford G3 panel of 83 clones was performed to further refine the map position of the hy7 gene. PCR amplification was carried out on this panel using primers hy7-A (5'GGATGGCCATTTGGAAAC3'; SEQ ID NO: 8) and hy7-B (5'CCAATCCTTCCATACATG3'; SEQ ID NO: 9), corresponding to nucleotides 507–524 and 890–907 of the hy7 cDNA (SEQ ID NO: 4), respectively.; The analysis indicated that the hy7 gene is most closely associated with the marker SHGC-418 on the long arm of chromosome 4. This map location is defined by markers AFM191xh2 and AFM347ZH1. Assessment of the flanking markers using the Whitehead/MIT STS-Based Map of the Human Genome) (World Wide Web URL: genome.wi.mit.edu/cgi-gin/contig/phys_map) in conjunction with The Genome Directory (Adams, M.D., et al. Nature 377 Suppl. (1995) identifies 4q21.3 as the most likely position of the hy7 gene.

Mouse Y7 Genomic DNA

Figure 3:
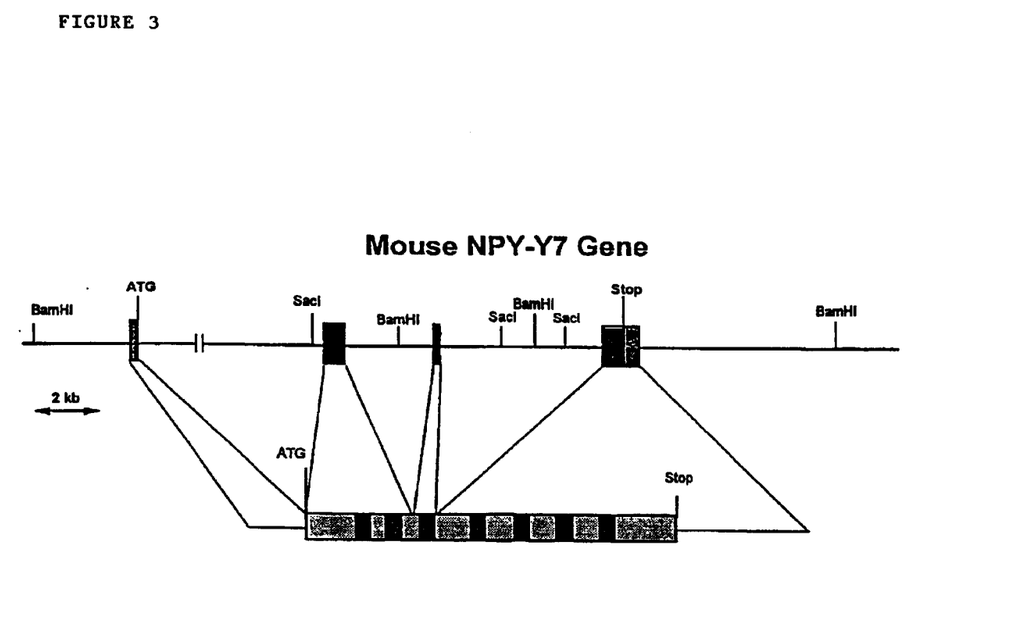
FIG. 3 provides a schematic diagram of the murine NPY-Y7 receptor gene. The gene covers approximately 12 kb and consists of three exons.

Using a $^{32}$P-labelled fragment of the hy7 cDNA a mouse genomic BAG library (Genome Systems) was screened. A clone encoding the entire gene of the mouse equivalent to hy7 was isolated (SEQ ID NO: 5). The gene covers approximately 12 kb and is divided by two introns into three exons (FIG. 3). FIG. 4 shows the degree of identity between the predicted amino acid sequence of the human and murine NPY-Y7 receptors.

Pharmacological Characterisation pcDNA3.1-hy7 cDNA was transiently transfected into the COSm6 cell line using FUGENE and 5 mg of DNA/106 cells. The COSm6 cells were grown in Dulbecco's modified Eagles medium supplemented with 2 mM glutamine and 10% fetal calf serum, in 5% $CO_2$ at 37° C. Membranes were harvested with COSm6 cells 72hr post-transfection. Adherent cells were washed twice in ice-cold phosphate buffered saline and lysed using a glass homogeniser in ice-cold hypotonic buffer (50 mM Tris-HCl, pH 7.4, 0.1% bacitracin). Membranes were pelleted by high speed centrifugation (30,000×g, 15 min 4° C.), homogeniser again in ice-cold hypotonic buffer and collected again by high speed centrifugation (30,000×g, 15 min, 4° C.). The final membrane pellet was resuspended into 1 ml of ice-cold binding buffer (50 mM Tris-HCl, pH7.4, 10 mM NaCl, 5 mM MgCl2, 2.5 mM CaCl2, 0.1% bacitracin, 0.1% bovine serum albumin. Membrane suspensions were diluted in binding buffer to yield membrane protein concentrations of 0.05 mg/ml. Under these conditions non-specific binding of [$^{125}$I] PYY to membranes was less than 10%. [$^{125}$I]PYY and unlabelled peptide competitors were also diluted to the required concentrations in binding buffer. Samples were prepared by mixing 50 ml binding buffer, unlabelled peptide or binding buffer (50 ml), [$^{125}$I]PYY (50 mM, 50 ml) and membrane suspension (100 ml). Samples were incubated at room temperature for 2hr. Incubations were terminated by centrifugation (4 min) and pellets collected. Radioactivity was measured for 1 min in a g counter.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. An isolated polynucleotide molecule encoding an NPY-Y7 receptor of human origin that comprises the amino acid sequence set forth in SEQ ID NO: 2.

2. An isolated polynucleotide molecule encoding an NPY-Y7 receptor, wherein the polynucleotide molecule comprises a nucleotide sequence selected from the group consisting of:
   (i) the sequence set forth in SEQ ID NO: 4;
   (ii) The sequence consisting of nucleotides 369 to 1592 of SEQ ID NO: 4; and
   (iii) a sequence that encodes the amino acid sequence set forth In SEQ ID NO: 2.

3. A plasmid or expression vector including the polynucleotide molecule according to claim 1.

4. A host cell transformed with the polynucleotide molecule according to claim 1.

5. The host cell according to claim 4, wherein said host cell is a mammalian or insect cell.

6. The host cell according to claim 5, wherein said host cell is a Chinese hamster ovary (CHO) cell, human embryonic kidney (HEK) 293 cell or an insect Sf9 cell.

7. The host cell according to claim 4, wherein said host cell expresses the NPY-Y7 receptor onto the cell's surface.

8. A host cell transformed with the plasmid or expression vector according to claim 3.

9. The host cell according to claim 8, wherein said host cell is a mammalian or insect cell.

10. The host cell according to claim 9, wherein said host cell is a Chinese hamster ovary (CHO) cell, human embryonic kidney (HEK) 293 cell or an insect Sf9 cell.

11. The host cell according to claim 8, wherein said host cell expresses the NPY-Y7 receptor onto the cell's surface.

* * * * *

SEQUENCE LISTING

```
<160> NUMBER OF SEQ ID NOS: 9

<210> SEQ ID NO 1
<211> LENGTH: 14
<212> TYPE: PRT
<213> ORGANISM: NPY-Y7 N-terminal consensus sequence
<220> FEATURE:
<221> NAME/KEY: MISC_FEATURE
<222> LOCATION: (2)..(3)
<223> OTHER INFORMATION: Xaa at position 2 is any amino acid; Xaa at
      position 3 is any amino acid
<220> FEATURE:
<221> NAME/KEY: MISC_FEATURE
<222> LOCATION: (5)..(5)
<223> OTHER INFORMATION: Xaa at position 5 is any amino acid
<220> FEATURE:
<221> NAME/KEY: MISC_FEATURE
<222> LOCATION: (10)..(10)
<223> OTHER INFORMATION: Xaa at position 10 is any amino acid

<400> SEQUENCE: 1

Met Xaa Xaa Met Xaa Glu Lys Trp Asp Xaa Asn Ser Ser Glu
1               5                   10

<210> SEQ ID NO 2
<211> LENGTH: 408
<212> TYPE: PRT
<213> ORGANISM: Homo sapiens NPY-Y7 receptor

<400> SEQUENCE: 2

Met Phe Ile Met Asn Glu Lys Trp Asp Thr Asn Ser Ser Glu Asn Trp
1               5                   10                  15

His Pro Ile Trp Asn Val Asn Asp Thr Lys His His Leu Tyr Ser Asp
            20                  25                  30

Ile Asn Ile Thr Tyr Val Asn Tyr Tyr Leu His Gln Pro Gln Val Ala
        35                  40                  45

Ala Ile Phe Ile Ile Ser Tyr Phe Leu Ile Phe Phe Leu Cys Met Met
    50                  55                  60

Gly Asn Thr Val Val Cys Phe Ile Val Met Arg Asn Lys His Met His
65                  70                  75                  80
```

Thr Val Thr Asn Leu Phe Ile Leu Asn Leu Ala Ile Ser Asp Leu Leu
                85                  90                  95

Val Gly Ile Phe Cys Met Pro Ile Thr Leu Leu Asp Asn Ile Ile Ala
            100                 105                 110

Gly Trp Pro Phe Gly Asn Thr Met Cys Lys Ile Ser Gly Leu Val Gln
            115                 120                 125

Gly Ile Ser Val Ala Ala Ser Val Phe Thr Leu Val Ala Ile Ala Val
            130                 135                 140

Asp Arg Phe Gln Cys Val Val Tyr Pro Phe Lys Pro Lys Leu Thr Ile
145                 150                 155                 160

Lys Thr Ala Phe Val Ile Ile Met Ile Ile Trp Val Leu Ala Ile Thr
                165                 170                 175

Ile Met Ser Pro Ser Ala Val Met Leu His Val Gln Glu Glu Lys Tyr
                180                 185                 190

Tyr Arg Val Arg Leu Asn Ser Gln Asn Lys Thr Ser Pro Val Tyr Trp
            195                 200                 205

Cys Arg Glu Asp Trp Pro Asn Gln Glu Met Arg Lys Ile Tyr Thr Thr
210                 215                 220

Val Leu Phe Ala Asn Ile Tyr Leu Ala Pro Leu Ser Leu Ile Val Ile
225                 230                 235                 240

Met Tyr Gly Arg Ile Gly Ile Ser Leu Phe Arg Ala Ala Val Pro His
                245                 250                 255

Thr Gly Arg Lys Asn Gln Glu Gln Trp His Val Val Ser Arg Lys Lys
            260                 265                 270

Gln Lys Ile Ile Lys Met Leu Leu Ile Val Ala Leu Leu Phe Ile Leu
            275                 280                 285

Ser Trp Leu Pro Leu Trp Thr Leu Met Met Leu Ser Asp Tyr Ala Asp
    290                 295                 300

Leu Ser Pro Asn Glu Leu Gln Ile Ile Asn Ile Tyr Ile Tyr Pro Phe
305                 310                 315                 320

Ala His Trp Leu Ala Phe Gly Asn Ser Ser Val Asn Pro Ile Ile Tyr
                325                 330                 335

Gly Phe Phe Asn Glu Asn Phe Arg Arg Gly Phe Gln Glu Ala Phe Gln
            340                 345                 350

Leu Gln Leu Cys Gln Lys Arg Ala Lys Pro Met Glu Ala Tyr Thr Leu
            355                 360                 365

Lys Ala Lys Ser His Val Leu Ile Asn Thr Ser Asn Gln Leu Val Gln
370                 375                 380

Glu Ser Thr Phe Gln Asn Pro His Gly Glu Thr Leu Leu Tyr Arg Lys
385                 390                 395                 400

Ser Ala Glu Asn Pro Asn Arg Asn
                405

<210> SEQ ID NO 3
<211> LENGTH: 405
<212> TYPE: PRT
<213> ORGANISM: Mus musculus NPY-Y7 receptor

<400> SEQUENCE: 3

Met Ser Thr Met Ser Glu Lys Trp Asp Ser Asn Ser Glu Ser Trp
1               5                   10                  15

Asn His Ile Trp Ser Gly Asn Asp Thr Gln His His Trp Tyr Ser Asp
            20                  25                  30

Ile Asn Ile Thr Tyr Val Asn Tyr Tyr Leu His Gln Pro Gln Val Ala

```
                35                  40                  45
Ala Val Phe Ile Ser Ser Tyr Leu Leu Ile Phe Val Leu Cys Met Val
         50                  55                  60

Gly Asn Thr Val Val Cys Phe Ile Val Ile Arg Asn Arg His Met His
 65                  70                  75                  80

Thr Val Thr Asn Phe Leu Ile Leu Asn Leu Ala Ile Ser Asp Leu Leu
                 85                  90                  95

Val Gly Ile Phe Cys Met Pro Ile Thr Leu Leu Asp Asn Ile Ile Ala
             100                 105                 110

Gly Trp Pro Phe Gly Ser Ser Met Cys Lys Ile Ser Gly Leu Val Gln
         115                 120                 125

Gly Ile Ser Val Ala Ala Ser Val Phe Thr Leu Val Ala Ile Ala Val
     130                 135                 140

Asp Arg Phe Arg Cys Val Val Tyr Pro Phe Lys Pro Lys Leu Thr Val
145                 150                 155                 160

Lys Thr Ala Phe Val Thr Ile Val Ile Ile Trp Gly Leu Ala Ile Ala
                165                 170                 175

Ile Met Thr Pro Ser Ala Ile Met Leu His Val Gln Glu Glu Lys Tyr
            180                 185                 190

Tyr Arg Val Arg Leu Ser Ser His Asn Lys Thr Ser Thr Val Tyr Trp
        195                 200                 205

Cys Arg Glu Asp Trp Pro Arg His Glu Met Arg Arg Ile Tyr Thr Thr
210                 215                 220

Val Leu Phe Ala Ile Ile Tyr Leu Ala Pro Leu Ser Leu Ile Val Ile
225                 230                 235                 240

Met Tyr Ala Arg Ile Gly Ala Ser Leu Phe Lys Thr Ala Ala His Cys
                245                 250                 255

Thr Gly Lys Gln Arg Pro Val Gln Cys Met Tyr Gln Glu Lys Gln Lys
            260                 265                 270

Val Ile Lys Met Leu Leu Thr Val Ala Leu Leu Phe Ile Leu Ser Trp
        275                 280                 285

Leu Pro Leu Trp Thr Leu Met Met Leu Ser Asp Tyr Thr Asp Leu Ser
    290                 295                 300

Pro Asn Lys Leu Arg Ile Ile Asn Ile Tyr Ile Tyr Pro Phe Ala His
305                 310                 315                 320

Trp Leu Ala Phe Cys Asn Ser Ser Val Asn Pro Ile Ile Tyr Gly Phe
                325                 330                 335

Phe Asn Glu Asn Phe Arg Asn Gly Phe Gln Asp Ala Phe Gln Ile Cys
            340                 345                 350

Gln Lys Lys Ala Lys Pro Gln Glu Ala Tyr Ser Leu Arg Ala Lys Arg
        355                 360                 365

Asn Ile Val Ile Asn Thr Ser Gly Leu Leu Val Gln Glu Pro Val Ser
370                 375                 380

Gln Asn Pro Gly Gly Glu Asn Leu Gly Cys Gly Lys Ser Ala Asp Asn
385                 390                 395                 400

Pro His Arg Asn Pro
            405

<210> SEQ ID NO 4
<211> LENGTH: 1903
<212> TYPE: DNA
<213> ORGANISM: Homo sapiens NPY-Y7-encoding gene

<400> SEQUENCE: 4
```

-continued

| | |
|---|---|
| ctcgagatcc attgtgctct aaaggcctcc tgagtagctg ggactacagg cgcccgccac | 60 |
| cacgcctggc taattttttt gtattttag tagggacggc gtttcactgt gttagccaga | 120 |
| tggtctccat ctcccgacct cgtgatccac ccacctcggc ctcccaaagt gctgggatta | 180 |
| caggcgtgag accgcgcccg gccaatttcc tttcttagtt gcctctgccc acctcttctc | 240 |
| ttctgcttcc atattacagg tttcctcagt tgcgaaatta ggatgttaat tatagctttt | 300 |
| gacatacaag aaacatcaaa aagattgaat gtcttaataa gagtgaagca tgtagatcag | 360 |
| tgactgctat gttcatcatg aatgagaaat gggacacaaa ctcttcagaa aactggcatc | 420 |
| ccatctggaa tgtcaatgac acaaagcatc atctgtactc agatattaat attacctatg | 480 |
| tgaactacta tcttcaccag cctcaagtgg cagcaatctt cattatttcc tactttctga | 540 |
| tcttcttttt gtgcatgatg ggaaatactg tggtttgctt tattgtaatg aggaacaaac | 600 |
| atatgcacac agtcactaat ctcttcatct aaacctggc cataagtgat ttactagttg | 660 |
| gcatattctg catgcctata acactgctgg acaatattat agcaggatgg ccatttggaa | 720 |
| acacgatgtg caagatcagt ggattggtcc agggaatatc tgtcgcagct tcagtcttta | 780 |
| cgttagttgc aattgctgta gataggttcc agtgtgtggt ctacccttt aaaccaaagc | 840 |
| tcactatcaa gacagcgttt gtcattatta tgatcatctg ggtcctagcc atcaccatta | 900 |
| tgtctccatc tgcagtaatg ttacatgtgc aagaagaaaa atattaccga gtgagactca | 960 |
| actcccagaa taaaaccagt ccagtctact ggtgccggga agactggcca aatcaggaaa | 1020 |
| tgaggaagat ctacaccact gtgctgtttg ccaacatcta cctggctccc ctctcccctca | 1080 |
| ttgtcatcat gtatggaagg attggaattt cactcttcag ggctgcagtt cctcacacag | 1140 |
| gcaggaagaa ccaggagcag tggcacgtgg tgtccaggaa gaagcagaag atcattaaga | 1200 |
| tgctcctgat tgtggccctg ctttttattc tctcatggct gccctgtgg actctaatga | 1260 |
| tgctctcaga ctacgctgac ctttctccaa atgaactgca gatcatcaac atctacatct | 1320 |
| acccttttgc acactggctg gcattcggca acagcagtgt caatcccatc atttatggtt | 1380 |
| tcttcaacga gaatttccgc cgtggtttcc aagaagcttt ccagctccag ctctgccaaa | 1440 |
| aaagagcaaa gcctatggaa gcttataccc taaaagctaa aagccatgtg ctcataaaca | 1500 |
| catctaatca gcttgtccag gaatctacat ttcaaaaccc tcatgggaa accttgcttt | 1560 |
| ataggaaaag tgctgaaaac cccaacagga attagtgatg aagaattaa aagaaactac | 1620 |
| taacagcagt gagatttaaa aagagctagt gtgataatcc taactctact acgcattata | 1680 |
| tatttaaatc cattgctttt tgtggctttg cacttcaaat ttttcaaaga atgttctaaa | 1740 |
| taaaacattt actgaaagcc ctctctggca aaaaattaa aaataaacaa aaatggtcat | 1800 |
| aagatcataa acaatcttat gttgtataaa aatacgtaga gtgacttaga catgtttgca | 1860 |
| tgaataaata tatttctaga gaacagttaa aaaaaaaaa aaa | 1903 |

<210> SEQ ID NO 5
<211> LENGTH: 1228
<212> TYPE: DNA
<213> ORGANISM: Mus musculus NPY-Y7-encoding gene

<400> SEQUENCE: 5

| | |
|---|---|
| atgtccacca tgagcgagaa atgggactca aactcttcag aaagctggaa tcacatctgg | 60 |
| agtggcaatg atacacagca tcactggtat tcagatatca acattaccta tgtgaactac | 120 |
| tatctccacc agccccaagt ggcagctgtc ttcatcagct cctacctcct gatctttgtc | 180 |
| ttgtgcatgg tgggaaatac tgtcgtttgc tttattgtga taaggaatag acacatgcac | 240 |

-continued

```
acagtcacta atttcttgat cttaaacctt gccataagtg atttactggt tggaatattc      300
tgtatgccta tcacattgct ggacaacatc atagcaggat ggccattcgg aagcagcatg      360
tgcaagatca gtgggctggt gcaagggata tcagttgcgg cttccgtctt caccttggtt      420
gcaatagctg tggacagatt ccgctgtgtg gtctacccct ttaagccaaa gctcactgtc      480 aagcagcct ttgtcacgat tgtgatcatc tggggcctgg ccatcgccat tatgactcca      540
```
(note: line above may have OCR errors)

Corrected reading:
```
acagtcacta atttcttgat cttaaacctt gccataagtg atttactggt tggaatattc      300
tgtatgccta tcacattgct ggacaacatc atagcaggat ggccattcgg aagcagcatg      360
tgcaagatca gtgggctggt gcaagggata tcagttgcgg cttccgtctt caccttggtt      420
gcaatagctg tggacagatt ccgctgtgtg gtctacccct ttaagccaaa gctcactgtc      480
aagcagcct ttgtcacgat tgtgatcatc tggggcctgg ccatcgccat tatgactcca      540
tctgcaataa tgttacatgt acaagaagaa aaatactacc gtgtgagact cagctcccac      600
aataaaacca gcacagtcta ctggtgtcgg gaggactggc caagacacga aatgaggagg      660
atctatacca cggtgctatt tgccatcatc tatcttgctc ctctctcact cattgttatc      720
atgtatgcaa ggattggggc ttccctcttc aagacggcag cacactgcac aggcaagcag      780
cgtccagtgc agtgcatgta tcaagagaaa cagaaggtca tcaagatgct gctgactgtg      840
gccctccttt tcatcctttc ctggcttccc ctgtggaccc tgatgatgct ctcagactat      900
actgacctgt ctcctaacaa actgcgtatc atcaacatct acatctaccc tttcgcccac      960
tggctcgcct tctgcaacag cagtgtcaac cctattattt atggattctt taatgaaaat     1020
tttcgcaatg gtttccaaga tgctttccag atctgccaaa agaaagccaa gccccaggaa     1080
gcctattccc tgagagcgaa acgcaacata gtcataaaca catcgggcct gctggtgcag     1140
gaaccggtgt ctcaaaaccc aggtggggaa aatttgggat gtggaaaaag tgcagacaat     1200
ccacacagga atccttgata gaggaatg                                        1228
```

<210> SEQ ID NO 6
<211> LENGTH: 384
<212> TYPE: PRT
<213> ORGANISM: human NPY-Y1 protein

<400> SEQUENCE: 6

```
Met Asn Ser Thr Leu Phe Ser Gln Val Glu Asn His Ser Val His Ser
1               5                   10                  15

Asn Phe Ser Glu Lys Asn Ala Gln Leu Leu Ala Phe Glu Asn Asp Asp
                20                  25                  30

Cys His Leu Pro Leu Ala Met Ile Phe Thr Leu Ala Leu Ala Tyr Gly
            35                  40                  45

Ala Val Ile Ile Leu Gly Val Ser Gly Asn Leu Ala Leu Ile Ile Ile
        50                  55                  60

Ile Leu Lys Gln Lys Glu Met Arg Asn Val Thr Asn Ile Leu Ile Val
65                  70                  75                  80

Asn Leu Ser Phe Ser Asp Leu Leu Val Ala Ile Met Cys Leu Pro Phe
                85                  90                  95

Thr Phe Val Tyr Thr Leu Met Asp His Trp Val Phe Gly Glu Ala Met
            100                 105                 110

Cys Lys Leu Asn Pro Phe Val Gln Cys Val Ser Ile Thr Val Ser Ile
            115                 120                 125

Phe Ser Leu Val Leu Ile Ala Val Glu Arg His Gln Leu Ile Ile Asn
        130                 135                 140

Pro Arg Gly Trp Arg Pro Asn Asn Arg His Ala Tyr Val Gly Ile Ala
145                 150                 155                 160

Val Ile Trp Val Leu Ala Val Ala Ser Ser Leu Pro Phe Leu Ile Tyr
                165                 170                 175

Gln Val Met Thr Asp Glu Pro Phe Gln Asn Val Thr Leu Asp Ala Tyr
            180                 185                 190
```

-continued

```
Lys Asp Lys Tyr Val Cys Phe Asp Gln Phe Pro Ser Asp Ser His Arg
            195                 200                 205
Leu Ser Tyr Thr Thr Leu Leu Val Leu Gln Tyr Phe Gly Pro Leu
    210                 215                 220
Cys Phe Ile Phe Ile Cys Tyr Phe Lys Ile Tyr Ile Arg Leu Lys Arg
225                 230                 235                 240
Arg Asn Asn Met Met Asp Lys Met Arg Asp Asn Lys Tyr Arg Ser Ser
                245                 250                 255
Glu Thr Lys Arg Ile Asn Ile Met Leu Leu Ser Ile Val Val Ala Phe
                260                 265                 270
Ala Val Cys Trp Leu Pro Leu Thr Ile Phe Asn Thr Val Phe Asp Trp
            275                 280                 285
Asn His Gln Ile Ile Ala Thr Cys Asn His Asn Leu Leu Phe Leu Leu
    290                 295                 300
Cys His Leu Thr Ala Met Ile Ser Thr Cys Val Asn Pro Ile Phe Tyr
305                 310                 315                 320
Gly Phe Leu Asn Lys Asn Phe Gln Arg Asp Leu Gln Phe Phe Phe Asn
                325                 330                 335
Phe Cys Asp Phe Arg Ser Arg Asp Asp Tyr Glu Thr Ile Ala Met
                340                 345                 350
Ser Thr Met His Thr Asp Val Ser Lys Thr Ser Leu Lys Gln Ala Ser
            355                 360                 365
Pro Val Ala Phe Lys Lys Ile Asn Asn Asn Asp Asn Glu Lys Ile
    370                 375                 380

<210> SEQ ID NO 7
<211> LENGTH: 381
<212> TYPE: PRT
<213> ORGANISM: human NPY-Y2 protein

<400> SEQUENCE: 7

Met Gly Pro Ile Gly Ala Glu Ala Asp Glu Asn Gln Thr Val Glu Glu
1               5                   10                  15
Met Lys Val Glu Gln Tyr Gly Pro Gln Thr Thr Pro Arg Gly Glu Leu
                20                  25                  30
Val Pro Asp Pro Glu Pro Glu Leu Ile Asp Ser Thr Lys Leu Ile Glu
            35                  40                  45
Val Gln Val Val Leu Ile Leu Ala Tyr Cys Ser Ile Ile Leu Leu Gly
    50                  55                  60
Val Ile Gly Asn Ser Leu Val Ile His Val Val Ile Lys Phe Lys Ser
65                  70                  75                  80
Met Arg Thr Val Thr Asn Phe Phe Ile Ala Asn Leu Ala Val Ala Asp
                85                  90                  95
Leu Leu Val Asn Thr Leu Cys Leu Pro Phe Thr Leu Thr Tyr Thr Leu
                100                 105                 110
Met Gly Glu Trp Lys Met Gly Pro Val Leu Cys His Leu Val Pro Tyr
            115                 120                 125
Ala Gln Gly Leu Ala Val Gln Val Ser Thr Ile Thr Leu Thr Val Ile
    130                 135                 140
Ala Leu Asp Arg His Arg Cys Ile Val Tyr His Leu Glu Ser Lys Ile
145                 150                 155                 160
Ser Lys Arg Ile Ser Phe Leu Ile Ile Gly Leu Ala Trp Gly Ile Ser
                165                 170                 175
Ala Leu Leu Ala Ser Pro Leu Ala Ile Phe Arg Glu Tyr Ser Leu Ile
            180                 185                 190
```

-continued

```
Glu Ile Ile Pro Asp Phe Glu Ile Val Ala Cys Thr Glu Lys Trp Pro
        195                 200                 205
Gly Glu Glu Lys Ser Ile Tyr Gly Thr Val Tyr Ser Leu Ser Ser Leu
        210                 215                 220
Leu Ile Leu Tyr Val Leu Pro Leu Gly Ile Ile Ser Phe Ser Tyr Thr
225                 230                 235                 240
Arg Ile Trp Ser Lys Leu Lys Asn His Val Ser Pro Gly Ala Ala Asn
                245                 250                 255
Asp His Tyr His Gln Arg Arg Gln Lys Thr Thr Lys Met Leu Val Cys
                260                 265                 270
Val Val Val Val Phe Ala Val Ser Trp Leu Pro Leu His Ala Phe Gln
        275                 280                 285
Leu Ala Val Asp Ile Asp Ser Gln Val Leu Asp Leu Lys Glu Tyr Lys
        290                 295                 300
Leu Ile Phe Thr Val Phe His Ile Ile Ala Met Cys Ser Thr Phe Ala
305                 310                 315                 320
Asn Pro Leu Leu Tyr Gly Trp Met Asn Ser Asn Tyr Arg Lys Ala Phe
                325                 330                 335
Leu Ser Ala Phe Arg Cys Glu Gln Arg Leu Asp Ala Ile His Ser Glu
                340                 345                 350
Val Ser Val Thr Phe Lys Ala Lys Lys Asn Leu Glu Val Arg Lys Asn
        355                 360                 365
Ser Gly Pro Asn Asp Ser Phe Thr Glu Ala Thr Asn Val
        370                 375                 380

<210> SEQ ID NO 8
<211> LENGTH: 18
<212> TYPE: DNA
<213> ORGANISM: primer hy7-A

<400> SEQUENCE: 8
ggatggccat ttggaaac                                              18

<210> SEQ ID NO 9
<211> LENGTH: 18
<212> TYPE: DNA
<213> ORGANISM: primer hy7-B

<400> SEQUENCE: 9
ccaatccttc catacatg                                              18
```